US009161734B2

(12) United States Patent
Vincent et al.

(10) Patent No.: US 9,161,734 B2
(45) Date of Patent: Oct. 20, 2015

(54) METHOD AND SYSTEM FOR FILTERING IMAGE DATA AND USE THEREOF IN VIRTUAL ENDOSCOPY

(75) Inventors: Thomas Bernard Pascal Vincent, Brossard (CA); Florent Andre Robert Chandelier, Montreal (CA)

(73) Assignee: CADENS MEDICAL IMAGING INC., Granby, Quebec (CA)

( * ) Notice: Subject to any disclaimer, the term of this patent is extended or adjusted under 35 U.S.C. 154(b) by 624 days.

(21) Appl. No.: 13/512,197

(22) PCT Filed: Nov. 27, 2009

(86) PCT No.: PCT/CA2009/001743
§ 371 (c)(1),
(2), (4) Date: May 25, 2012

(87) PCT Pub. No.: WO2011/063493
PCT Pub. Date: Jun. 3, 2011

(65) Prior Publication Data
US 2012/0296771 A1 Nov. 22, 2012

(51) Int. Cl.
*G06K 9/00* (2006.01)
*A61B 6/00* (2006.01)
(Continued)

(52) U.S. Cl.
CPC . *A61B 6/50* (2013.01); *A61B 5/055* (2013.01); *A61B 5/4255* (2013.01); *A61B 6/506* (2013.01);
(Continued)

(58) Field of Classification Search
None
See application file for complete search history.

(56) References Cited

U.S. PATENT DOCUMENTS 5,832,134 A * 11/1998 Avinash et al. ............... 382/257
6,366,800 B1 * 4/2002 Vining et al. ................. 600/425
(Continued)

FOREIGN PATENT DOCUMENTS

WO WO2005088520 9/2005
WO WO2006084150 8/2006
(Continued)

OTHER PUBLICATIONS

Kniss et al. "Multidimensional Transfer Functions for Interactive Volume Rendering", IEEE Transactions on Visualization and Computer Graphics, vol. 8, No. 3, Jul.-Sep. 2002, pp. 270-285.*
(Continued)

*Primary Examiner* — Vu Le
*Assistant Examiner* — Samah Beg
(74) *Attorney, Agent, or Firm* — Pearl Cohen Zedek Latzer Baratz LLP

(57) ABSTRACT

A method for filtering image data having at least three types of distinct regions from a selected type of region, each of the at least three types of distinct regions being characterized by a plurality of unitary image elements, the method comprising providing the image data; selecting a portion of the image data comprising at least a corresponding portion of each of the at least three types of regions; determining at least one distribution for each of the at least three types of regions in the selected portion; determining at least one function for associating each unitary image element of the selected type of region in the selected portion to another type of region of the at least three types of regions such that the at least one distribution of the selected type of regions in the selected portion is transposed into a corresponding distribution of the another type of region; and applying the at least one function to each unitary image element of the selected type of region of the selected portion to thereby provide filtered image data. Applications of the method for suppressing tagged material in virtual colonoscopy are also disclosed.

25 Claims, 13 Drawing Sheets

(51) Int. Cl.
*A61B 5/055* (2006.01)
*A61B 5/00* (2006.01)
*G06T 7/00* (2006.01)
*A61B 8/13* (2006.01)

(52) U.S. Cl.
CPC ............ *G06T 7/0081* (2013.01); *G06T 7/0087* (2013.01); *A61B 6/505* (2013.01); *A61B 8/13* (2013.01); *G06T 2207/10081* (2013.01); *G06T 2207/30028* (2013.01)

(56) References Cited

U.S. PATENT DOCUMENTS

| | | | |
|---|---|---|---|
| 6,445,182 | B1 | 9/2002 | Dean |
| 8,611,622 | B2 * | 12/2013 | Vincent et al. ............... 382/128 |
| 8,848,995 | B2 * | 9/2014 | Delsanto et al. ............. 382/130 |
| 2004/0101183 | A1 * | 5/2004 | Mullick et al. ............... 382/131 |
| 2004/0164996 | A1 | 8/2004 | Criminisi |
| 2004/0252870 | A1 * | 12/2004 | Reeves et al. ................ 382/128 |
| 2007/0116347 | A1 * | 5/2007 | Hong ........................... 382/131 |
| 2008/0118133 | A1 * | 5/2008 | Sirohey et al. ............... 382/131 |
| 2008/0205717 | A1 * | 8/2008 | Reeves et al. ................ 382/128 |
| 2008/0273781 | A1 * | 11/2008 | Manduca et al. ............. 382/131 |
| 2009/0304248 | A1 * | 12/2009 | Zalis et al. ................... 382/131 |
| 2010/0080354 | A1 * | 4/2010 | Fu et al. ....................... 378/65 |
| 2012/0081386 | A1 * | 4/2012 | Wiemker et al. ............. 345/589 |
| 2012/0224760 | A1 * | 9/2012 | Goshen et al. ............... 382/131 |
| 2013/0195327 | A1 * | 8/2013 | Tanji ........................... 382/128 |

FOREIGN PATENT DOCUMENTS

| | | |
|---|---|---|
| WO | WO2007048091 | 4/2007 |
| WO | WO 2007064980 A2 * | 6/2007 |
| WO | WO2008149358 | 12/2008 |

OTHER PUBLICATIONS

Criminisi Antonio et al, Region Filling and Object Removal by Exemplar-Based Image Inpainting, Transitions on Image Processing, vol. 13, No. 9, Sep. 2004.
Augusto Silva et al, Fast Pulmonary Contour Extraction in X-ray CT Images: A Method and Quality Assessment SPIE: vol. 4321, 2001.
International Search Report for International Application No. PCT/CA2009/001743 mailed Aug. 27, 2010.

* cited by examiner

802

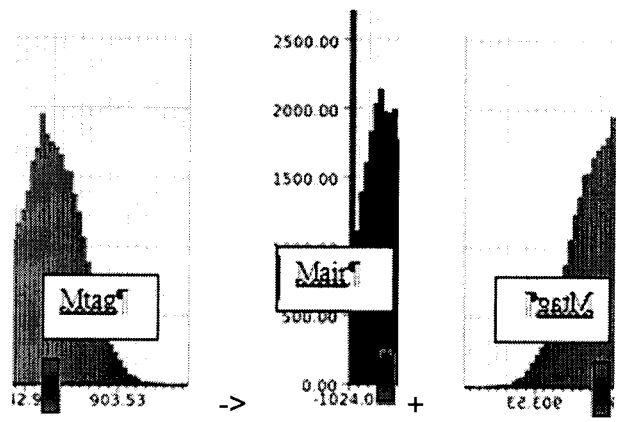
FIG. 10A
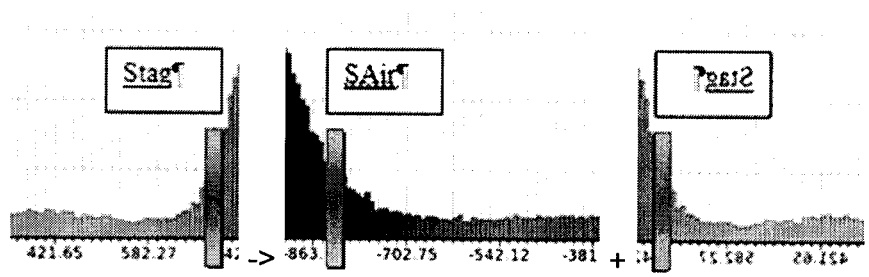
FIG. 10B
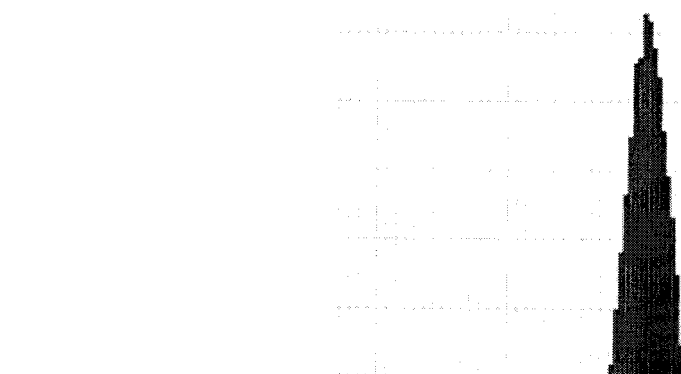
FIG. 10C
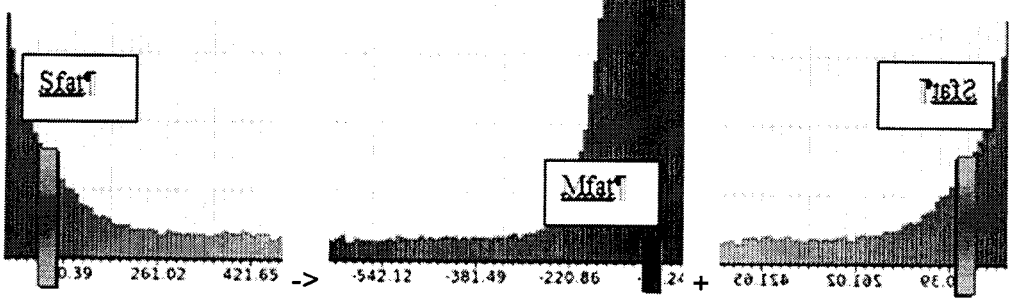

METHOD AND SYSTEM FOR FILTERING IMAGE DATA AND USE THEREOF IN VIRTUAL ENDOSCOPY

CROSS-REFERENCE TO RELATED APPLICATIONS

This application is a National Phase Application of PCT International Patent Application No. PCT/CA2009/001743, International Filing Date Nov. 27, 2009, which is incorporated herein by reference.

CROSS REFERENCE TO RELATED APPLICATION

The present application relates to PCT application entitled "Method and system for determining an estimation of a topological support of a tubular structure and use thereof in virtual endoscopy", the specification of which is incorporated herein by reference.

FIELD OF THE INVENTION

The invention generally relates to image processing and more particularly relates to a method and a system for filtering image data. It also relates to applications of the method for suppressing tagged material in virtual colonoscopy.

BACKGROUND OF THE INVENTION

Conventional endoscopic procedures typically rely on the use of a flexible fiber optic tube which is inserted in the patient's body to visually examine an inner anatomical structure. The operator can then manipulate the tube inside the anatomical structure to search for any anatomical abnormalities.

Conventional colonoscopies using this procedure, although reliable, are both costly in money and time. Moreover, it is an invasive, uncomfortable and sometimes painful procedure for the patient.

Non-invasive procedures have been used to reduce at least one of the above mentioned drawbacks of the invasive colonoscopic procedure.

These non-invasive procedures use imaging techniques such as a computed tomography (CT) scanning to obtain image data representative of the anatomical structure to analyze. These procedures nevertheless require a cathartic preparation of the patient for colon cleansing prior to the exam.

To even reduce the discomfort felt by the patient, minimum cathartic preparation procedures that tag liquid and solid fecal matter for subsequent virtual removal using digital subtraction algorithms have been proposed.

However, the imaging techniques used to obtain the image data typically present a spatial resolution which generates a blur at each anatomical interface.

Consequently, when removing the tagging material, these algorithms may artificially smooth the surface between the removed material and the colon's inner wall and polyps or other abnormalities present in the colon may be inadvertently removed or wrongly reduced to an acceptable level, which is a major concern.

These algorithms generally rely on image segmentation by using a threshold adapted for characterizing the interfaces of the structure under analysis.

However, since the different anatomical structures may be very different from each other, a simple threshold may not allow to conveniently segment a structure in a single pass. Indeed, soft tissues, bones and fat tissues have different densities.

In order to take into consideration this great variability of the structures, different techniques have been used. For example, PCT international applications published under publication numbers WO2008/089492, WO2007/064980 and WO02/029764 and US patent applications published under publication numbers 2008/0118133 and 2008/0008367 teach various methods for electronic cleansing of medical images. However, they still use a threshold for structure segmentation and the resulting segmentation may still remain approximated for a plurality of unitary image elements. The interfaces between the different structures may then still be smoothed. This may lead an operator to a wrong diagnosis, which is a major issue.

U.S. Pat. No. 6,366,800 describes a method for automatic analysis in virtual endoscopy. This method however also relies on segmentation techniques and the resulting segmentation may still remain approximated.

It would therefore be desirable to provide an improved method for electronic cleansing of medical images that will reduce at least one of the above-mentioned drawbacks.

BRIEF SUMMARY

Accordingly, there is disclosed a method for filtering image data having at least three types of distinct regions from a selected type of region, each of the at least three types of distinct regions being characterized by a plurality of unitary image elements, the method comprising providing the image data; selecting a portion of the image data comprising at least a corresponding portion of each of the at least three types of regions; determining at least one distribution for each of the at least three types of regions in the selected portion; determining at least one function for associating each unitary image element of the selected type of region in the selected portion to another type of region of the at least three types of regions such that the at least one distribution of the selected type of regions in the selected portion is transposed into a corresponding distribution of the another type of region; and applying the at least one function to each unitary image element of the selected type of region of the selected portion to thereby provide filtered image data.

The filtering of the selected type of region is obtained without segmenting any regions, which is of great advantage, particularly in the case wherein the method is used as a pre-processing step prior to a subsequent processing.

In one embodiment, the providing of the image data comprises receiving the image data from a CT scanning device.

In another embodiment, the providing of the image data comprises receiving the image data from the group consisting of a magnetic resonance imaging (MRI) device, a positron emission tomography (PET) device, an X-Rays device, an ultrasound device and any combination thereof.

In one embodiment, the image data are selected from the group consisting of volumetric medical image data, volumetric tomographic image data and a set of parallel successive image planes.

In one embodiment, the image data comprises a plurality of unitary image elements selected from the group consisting of pixels and voxels.

In one embodiment, the image data are representative of an anatomic structure.

In a further embodiment, the anatomic structure comprises a portion of a colon.

In one embodiment, each of the at least three types of distinct regions respectively comprises a first substance type region, a second substance type region and a third substance type region.

In a further embodiment, each of the at least three types of distinct regions respectively comprises an air type region, a tagged substance type region and a biological tissues type region.

In still a further embodiment, the filtered image data comprise at least an air type region and a biological tissues type region.

In one embodiment, the selected portion of the image data comprises a corresponding region of the selected type of region.

In one embodiment, the selecting of a portion of the image comprises selecting one of the regions and selecting an immediate neighboring until a resulting area comprises the at least three types of regions.

In a further embodiment, the immediate neighboring is selected until the resulting area comprises a representative portion of each of the at least three types of regions.

In one embodiment, the determining of at least one distribution comprises determining an intensity distribution of a representative part of the unitary image elements corresponding to the selected portion.

In another embodiment, the determining of at least one distribution comprises determining a gradient distribution of a representative part of the unitary image elements corresponding to the selected portion.

In another embodiment, the determining of at least one distribution comprises determining an intensity derivative distribution of a representative part of the unitary image elements corresponding to the selected portion.

In a further embodiment, the determining of at least one distribution comprises determining a plurality of distributions selected from the group consisting of an intensity distribution of a representative part of the corresponding unitary image elements, a gradient distribution of a representative part of the corresponding unitary image elements and an intensity derivative distribution of a representative part of the corresponding unitary image elements.

In one embodiment, the determining of at least one function comprises determining an initial approximating function for approximating the corresponding distribution and determining a transposition function adapted for transposing the initial approximating function into the corresponding distribution of the another type of region.

In a further embodiment, the method further comprises determining an additional initial function for approximating the distribution of the another type of region, and wherein the applying of the at least one function comprises applying the transposition function to thereby transpose the initial function into the additional initial function.

In still a further embodiment, the initial approximating function is selected from the group consisting of a laplacian function and a gaussian function.

In another embodiment, each of the initial approximating function and the additional initial approximating function is selected from the group consisting of a laplacian function and a gaussian function.

In one embodiment, the determining of at least one function comprises determining at least one of a laplacian function and a gaussian function.

In one embodiment, the determining of at least one function comprises applying a Fourier transformation to the at least one distribution.

In another embodiment, the determining of at least one function comprises applying a parametric law to the at least one distribution.

In one embodiment, the method for filtering image data further comprises displaying the filtered image data.

In another embodiment, the method for filtering image data further comprises displaying a three dimensional rendering of the anatomic structure.

In still another embodiment, the method for filtering image data further comprises providing the filtered image data to a volume rendering engine for 3D visualization.

In one embodiment, the method for filtering image data further comprises providing the filtered image data to a computer-aided detection unit for abnormalities detection.

In another embodiment, the method for filtering image data further comprises providing the filtered image to a computer-aided diagnosis unit for anatomical abnormalities diagnosis.

In still another embodiment, the method for filtering image data further comprises providing the filtered image data to a volume rendering engine for 3D visualization.

In one embodiment, the method for filtering image data further comprises using the filtered image data for performing a virtual endoscopy.

For the particular application of electronic colon cleansing, the method enables the filtering of the tagged substance type regions from the image data, which is of great advantage.

According to another aspect, there is also provided a system for filtering image data having at least three types of distinct regions from a selected type of region, each of the at least three types of distinct regions being characterized by a plurality of unitary image elements. The system comprises a data receiving unit for receiving the image data and a selecting unit coupled to the data receiving unit for selecting a portion of the image data comprising at least a corresponding portion of each of the at least three types of regions and providing a selected portion of the image data. The system comprises a distribution determining unit coupled to one of the selecting unit and the data receiving unit for determining at least one distribution for each of the at least three types of regions in the selected portion and providing at least one determined distribution for each of the at least three types of regions in the selected portion. The system comprises a function determining unit coupled to the distribution determining unit for determining at least one function for associating each unitary image element of the selected type of region in the selected portion to another type of region of the at least three types of regions such that the at least one determined distribution of the selected type of regions in the selected portion is transposed into a corresponding distribution of the another type of region. The system also comprises a filtering unit coupled to the function determining unit for applying the at least one function to each unitary image element of the selected type of region of the selected portion to thereby provide filtered image data.

In one embodiment, the system further comprises a display unit coupled to the filtering unit for displaying the filtered image data to a user.

In one embodiment, the system further comprises a transmitting unit coupled to the filtering unit for transmitting the filtered image data to a computer-aided detection unit for abnormalities detection.

In another embodiment, the system further comprises a transmitting unit coupled to the filtering unit for transmitting the filtered image data to a computer-aided diagnosis unit for abnormalities diagnosis.

In another embodiment, the function determining unit comprises a first module for determining an initial approximating function to approximate the corresponding distribution and a second module for determining a transposition function adapted to transpose the initial approximating function into the corresponding distribution of the another type of region.

According to another aspect, there is disclosed the use of the system for filtering image data for performing a virtual endoscopy.

According to another aspect, there is disclosed the use of the system for filtering image data for suppressing tagged material in a virtual colonoscopy selected from the group consisting of a prepless CT colonoscopy, a laxative free CT colonoscopy, a mild preparation CT colonoscopy with tagging agent and a cathartic preparation with tagging of remnant fluids/stools for CT colonoscopy.

According to another aspect, there is disclosed the use of the method for filtering image data for suppressing tagged material in a virtual colonoscopy selected from the group consisting of a prepless CT colonoscopy, a laxative free CT colonoscopy, a mild preparation CT colonoscopy with tagging agent and a cathartic preparation with tagging of remnant fluids/stools for CT colonoscopy.

According to another aspect, there is also provided the use of the system for filtering image data for suppressing tagged material in a virtual colonoscopy involving Iodine-based tagging agents.

According to another aspect, there is also provided the use of the system for filtering image data for suppressing tagged material in a virtual colonoscopy involving Barium-based tagging agents.

According to another aspect, there is provided a machine readable medium having instructions recorded thereon for performing the method for filtering image data.

According to another aspect, there is also provided a method of doing business in filtering image data according to the method for filtering image data previously described, wherein the image data are filtered for a fee.

According to another aspect, there is also provided a method of doing business in filtering image data, the method comprising receiving the image data; performing the method for filtering image data as previously described; and providing the filtered image for a fee.

According to another aspect, there is also provided a method of doing business in filtering image data, the method comprising providing by a provider a system for filtering image data as previously described to a third party; operating the system, wherein the operating is done by a third party for a fee; and reconveying by the third party at least a portion of the fee to the provider.

According to another aspect, there is also provided a method of doing business in filtering image data, the method comprising providing a tagging agent; defining a tagging agent distribution associated to the tagging agent; providing a system for filtering image data wherein the system is customized according to the tagging agent distribution; performing the method for filtering image data as previously described wherein the image data are obtained with the tagging agent; and providing the filtered image for a fee.

According to another aspect, there is also provided a method of doing business in filtering image data, the method comprising providing a tagging agent; defining a tagging agent distribution associated to the tagging agent; providing by a provider a system for filtering image data to a third party, the system being customized according to the tagging agent distribution; operating the system, wherein the operating is done by a third party for a fee; and reconveying by the third party at least a portion of the fee to the provider.

The method for filtering image data is not limited to specific types of image data, which is of great advantage. Moreover, the method does not rely on predetermined rigorous values of the image data, which is also of great advantage. The method may thus be used with a wide variety of image data types and a wide variety of scanning devices.

Moreover, the method for filtering image data is well adapted for any anatomical structure comprising at least two phases, such as the colon structure which comprises an inner wall and a plurality of air regions and fecal matter regions extending therein, which is also of great advantage.

The skilled addressee will appreciate that for the particular application of colon electronic cleansing, the method enables to filter the tagged substance type regions from the image data without artificially smoothing the surface between the removed material and the colon's inner wall, which is of great advantage since it may enable a more accurate colorectal cancer screening.

Moreover, since the method does not artificially smooth any surfaces, the representation in 3D of any potential lesion may be enhanced, particularly for flat lesions or small lesions having a size of about 3 to 4 mm, which is also of great advantage for detecting potential lesion at an early stage.

The skilled addressee will also appreciate that the method does not rely on any a-priori or assumption on the morphology of the tubular structure, which is also of great advantage for providing an enhanced filtering.

The skilled addressee will also appreciate that the method is particularly advantageous for enhancing the 3D representation or the 2D representation of the information contained within the raw image data since the images have not to be segmented. This is a great advantage since a given operator may choose the 2D representation and/or the 3D representation to review the images.

The skilled addressee will also appreciate that the method may require shorter computational time for providing the filtered images than typical segmenting methods, which is also of great advantage.

The expression "region" means a set of neighboring unitary image elements which are all contiguous to each others in a same pocket. The regions may be in 2D or 3D, depending on the image data used.

BRIEF DESCRIPTION OF THE DRAWINGS

In order that the invention may be readily understood, embodiments of the invention are illustrated by way of example in the accompanying drawings.

FIG. 10A to 10C illustrate a transposition process according to one embodiment.

Figure 1:
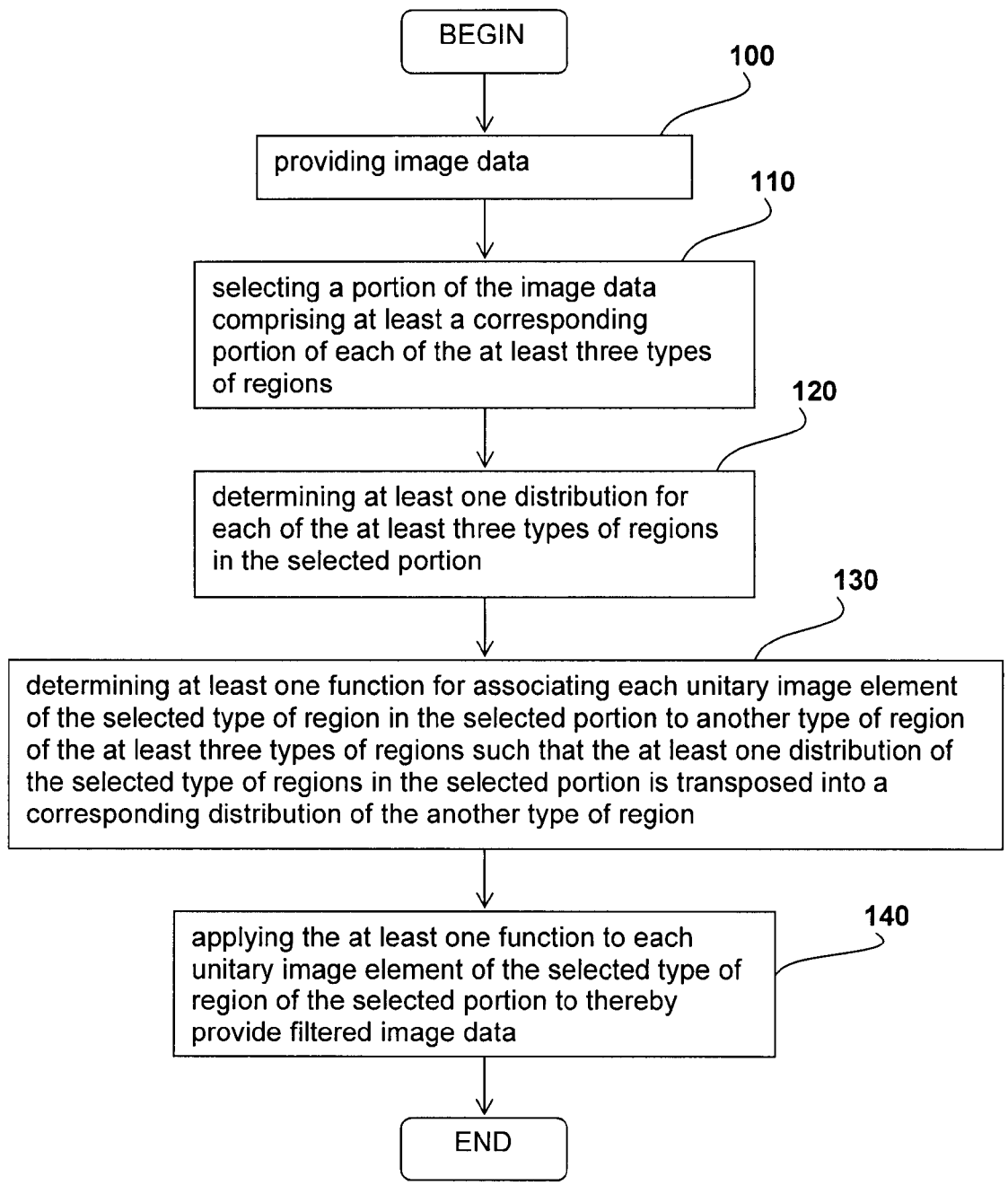
FIG. 1 is a flow chart of a method for filtering image data, according to one embodiment of the invention.

Further details of the invention and its advantages will be apparent from the detailed description included below.

DETAILED DESCRIPTION

In the following description of the embodiments, references to the accompanying drawings are by way of illustration of examples by which the invention may be practiced. It will be understood that various other embodiments may be made and used without departing from the scope of the invention disclosed.

The invention concerns a method and a system for filtering image data that are particularly useful for filtering medical images. Throughout the present description, the method will be described for the particular application of electronic colon cleansing in virtual colonoscopy but the skilled addressee will appreciate that the method is not limited to this specific application and that many other applications may be considered, as it will become apparent upon reading of the present description.

The method for filtering image data of the invention may be generally useful for facilitating the subsequent segmentation of an anatomical structure but is also well adapted for anatomical structure comprising at least two phases, such as the colon structure which comprises an inner wall and a plurality of air regions and fecal matter regions extending therein.

As it will become apparent below, in one embodiment, the method for filtering image data may be useful for examination of the colon, more specifically for colorectal cancer screening.

The method is particularly advantageous since it is not limited to specific types of image data. Rather, the method may be used on different types of image data sets, as it will become apparent upon reading of the present description.

Indeed, the skilled addressee will appreciate that the system and the method described above are particularly advantageous since they may be used with prepless CT colonoscopy, laxative free CT colonoscopy, mild preparation CT colonoscopy with tagging agent and cathartic preparation with tagging of remnant fluids/stools for CT colonoscopy as non limitative examples.

Prepless CT colonoscopy is described in Comparison of routine and unprepped CT colonography augmented by low fiber diet and stool tagging: a pilot study, Abraham H. Dachman and al., Abdom Imaging (2007) 32:96-104; in CT Colonography without Cathartic Preparation: Feasibility Study, Matthew R. Callstrom, Radiology 2001; 219:693-698 and also in CAD of Colon Cancer on CT Colonography Cases without Cathartic Bowel Preparation, Marius George Linguraru and al., 30th Annual International IEEE EMBS Conference Vancouver, British Columbia, Canada, Aug. 20-24, 2008. Each of these references is incorporated herein by reference.

Laxative free CT colonoscopy is described in Development of a Cathartic-Free Colorectal Cancer Screening Test Using Virtual Colonoscopy: A Feasibility Study, Kristina T. Johnson, AJR:188, January 2007, p 2936; in Dietary Fecal Tagging as a Cleansing Method before CT Colonography: Initial Results—Polyp Detection and Patient Acceptance1, Philippe A. Lefere, Radiology 2002; 224:393-403; and in Noncathartic CT Colonography with Stool Tagging: Performance With and Without Electronic Stool Subtraction, C. Daniel Johnson, AJR:190, February 2008, p 361-366. Each of these references is incorporated herein by reference.

Mild preparation CT colonoscopy with tagging agent is described in Image Quality and Patient Acceptance of Four Regimens with Different Amounts of Mild Laxatives for CT Colonography, Sebastiaan Jensch and al., AJR:191, July 2008, p 158-167, which is incorporated herein by reference.

Cathartic preparation with tagging of remnant fluids/stools for CT colonoscopy is described in Efficacy of Barium-Based Fecal Tagging for CT Colonography: a Comparison between the Use of High and Low Density Barium Suspensions in a Korean Population—a Preliminary Study, Min Ju Kim and al., Korean J Radiol 10(1), February 2009, p 25-33; in The Alternative: Faecal Tagging, Philippe Lefere and Stefaan Gryspeerdt, Virtual Colonoscopy, Springer Berlin Heidelberg, 2006, p 35-49; and in Tagging-based, Electronically Cleansed CT Colonography: Evaluation of Patient Comfort and Image Readability, Michael E. Zalis, and al., Radiology: Volume 239: Number 1—April 2006, p 149-159. Each of these references is incorporated herein by reference.

The skilled addressee will appreciate that laxative-free preparations may involve the use of Iodine that may have a potential laxative side-effect but may provide better residual tagging than barium only tagging preparations.

Moreover, the skilled addressee will appreciate that the disclosed method may enable to filter image data in a relative fast manner, depending on processing resources used.

Indeed, typically, such filtering method may be performed within 5 minutes on a Intel dual-core CPU, in one embodiment.

Current state-of-the-art methods typically require over 15 minutes, as presented in "Structure-analysis method for electronic cleansing in cathartic and noncathartic CT colonography", Wenli Cai and al., Med. Phys. 35(7), July 2008 p 3259-3277, wherein electronic cleansing is described as requiring approximately 30 minutes for the CTC images from a scan of a patient on a standard PC. In other words, one hour will be typically required for a complete CTC exam that includes 2 scans, namely the prone and the supine scans.

Figure 5A:
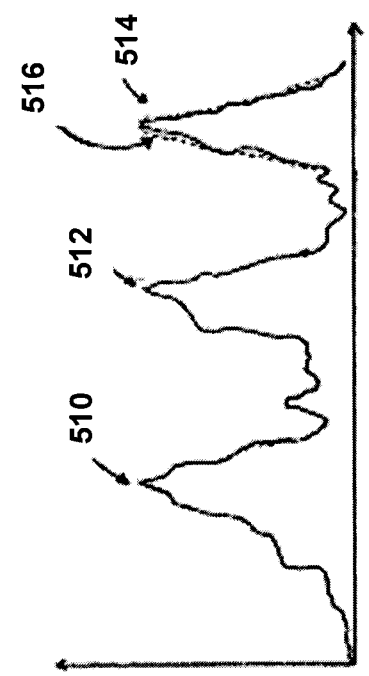
FIG. 5A is a schematic illustrating a sectional image of a colon having tagged substance type regions.

FIG. 5A illustrates the image data of an anatomical structure, more specifically a portion of a colon 500, having at least three types of distinct region, that is a biological tissues type region 502, an air type region 504 and two tagged substance type regions 506, 508 corresponding to tagged fecal matter, also generally referred to as the first substance type region, the second substance type region and the third substance type region.

Throughout the present description, the expression "region" means a set of neighboring unitary image elements which are all contiguous to each others in a same pocket. The regions may be in 2D or 3D, depending on the image data used, as it will become apparent below.

Moreover, by the expression "biological tissues type region", it is meant any portion of anatomical structures comprising soft tissues, fat, bones, connective tissues, nervous tissues, epithelial tissues and muscles as non-limitative examples. The skilled addressee will appreciate that in the specific case of colon examination, the biological tissues also comprise the mucosa of the colon.

Referring to FIG. 1, there is shown a flow chart of a method for filtering image data according to one embodiment. The method enables to filter image data having at least three types of distinct regions from a selected type of region, each of the at least three types of distinct regions being characterized by a plurality of unitary image elements. In one embodiment, each of the unitary image element comprises a pixel while in another embodiment, each of the unitary image element comprise a voxel. The skilled addressee will appreciate that the expression "unitary image elements" should not be limited to pixels and voxels but should rather be understood as encompassing any homogenous element, point or dot of an image or display surface or geometrical element to which an intensity, a color or another parameter may be associated individually to the others.

The skilled addressee will appreciate that for the particular application of electronic colon cleansing, the method enables to filter the tagged substance type regions from the image data, which is of great advantage, as it will be understood thereinafter.

According to processing step 100, the image data are provided. The image data may comprise, as non-limitative examples, a volumetric medical image, a volumetric tomographic image and/or a plurality of parallel successive image planes, as well known in the art and as detailed thereinafter.

In one embodiment, the processing step 100 may comprises receiving the image data from a CT scanning device.

In one embodiment, the image data may be received from a magnetic resonance imaging (MRI) device. Alternatively, the processing step 100 may comprise receiving the image data from a positron emission tomography (PET) device. In another embodiment, the image data may be received from an X-Rays device. In still another embodiment, the image data may be received from an ultrasound device or any combination of the above mentioned devices.

In a further embodiment, the image data may be retrieved from a database or may even be retrieved from a readable medium such as a compact disk or a picture archiving and communication system (PACS) for instance.

Still referring to FIG. 1, according to processing step 110, a portion of the image data comprising at least a corresponding portion of each of the at least three types of regions is selected.

In one embodiment, the selected portion of the image data comprises a corresponding region of the selected type of region, that is an entire tagged substance type region, such as region 508 of FIG. 5 for example. In a preferred embodiment, a typical region growing is used for selecting the entire region.

The skilled addressee will appreciate that, in prior art applications of region growing, the unitary image elements of a same region are grouped according to an iterative process based on their homogeneity, to thereby segment the selected portion of the image data into distinct zones of interest. In these prior art applications, the region growing is used to extract one particular region from the others.

For example, in US patent application published under number US 2002/0193687 and entitled Automatic analysis in virtual endoscopy, the region growing is explained as follows: the region of interest is segmented using a three-dimensional region growing technique and an initial static threshold value. The threshold value chosen should approach the maximum threshold value which can be selected without having the segmentation procedure fail by including surrounding structures as part of the region of interest.

The skilled addressee will understand upon reading of the present description that in the present application, the region growings are not used for purpose of segmenting an image into distinct zones of interest in order to extract a particular region. Rather, the region growings are used to select a part of an image surrounding a corresponding portion thereof. As previously described, the resulting area obtained from the region growing should comprise portions of several types of region.

In a further embodiment, the processing step 110 may further comprise selecting one of the regions and selecting an immediate neighboring thereof until a resulting area comprises the at least three types of regions. In a preferred embodiment, the selected immediate neighboring comprises portions of neighboring regions which are not of the same type of the selected region.

Moreover, still in a preferred embodiment, the immediate neighboring is selected until the resulting area comprises a representative portion of each of the at least three types of regions.

In other words, in a preferred embodiment, a tagged substance type region is first selected, and then the immediate neighboring is selected until the entire selected tagged substance type region is included in the resulting area and until the resulting area also comprises a portion of an air type region and a portion of a biological tissues type region. In a preferred embodiment, each of the portions of the different regions comprised in the resulting area may be large enough so as to be representative of the corresponding regions, as it will be understood thereinafter.

It should nevertheless be appreciated that, in one embodiment, the immediate neighboring selected may not comprise another region of the same type that the region of interest nor bones since these regions may affect the corresponding distributions.

The skilled addressee will appreciate that the selecting of an immediate neighboring may be performed on volumetric image data. Thus, it should be understood that the resulting area may be a three dimensional volume obtained on a plurality of consecutive two dimensional images, as it will be explained below.

Still referring to FIG. 1, according to processing step 120, at least one distribution for each of the at least three types of regions in the selected portion is determined.

In one embodiment, the determining of at least one distribution comprises determining an intensity distribution of a representative part of the unitary image elements corresponding to the selected portion. In a further embodiment, each of the unitary image elements corresponding to the selected portion may be considered. However, selecting a representative part only may be advantageous since it may help and/or speed up the subsequent processing, as it will become apparent thereinafter. For example, the unitary image elements whose intensity is above a given value may be selected.

Figure 5B:
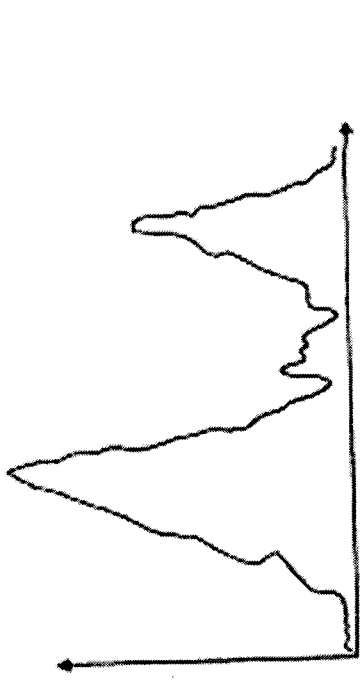
FIG. 5B is a schematic of the intensity distribution of the sectional image of FIG. 5A.

FIG. 5B schematically shows the intensity distribution of the image data shown in FIG. 5A. As illustrated, the intensity distribution comprises a first peak 510 corresponding to the air type region 504, a second peak 512 corresponding to the biological tissues type region 502 and a third peak 514 corresponding to the tagged substance type regions 506 and 508.

In another embodiment, the determining of at least one distribution comprises determining a gradient distribution of a representative part of the unitary image elements corresponding to the selected portion. As previously mentioned, in one embodiment, each of the unitary image elements corresponding to the selected portion may be considered.

In another embodiment, the determining of at least one distribution comprises determining an intensity derivative distribution of a representative part of the unitary image elements corresponding to the selected portion. As previously mentioned, in one embodiment, each of the unitary image elements corresponding to the selected portion may be considered.

In a further embodiment, the determining of at least one distribution may comprise determining a plurality of distributions. In such a case and according to a specific application, the plurality of distributions may be selected from the group consisting of an intensity distribution of a representative part of the corresponding unitary image elements, a gradient distribution of a representative part of the corresponding unitary image elements and an intensity derivative distribution of a representative part of the corresponding unitary image elements. The skilled addressee will appreciate that using a plurality of distributions may be advantageous in particular cases, as described in "Multidimensional transfer functions for interactive volume rendering", Kniss, J. Kindlmann, G. Hansen, C. Sci. Comput. & Image Inst., Utah Univ., Salt Lake City, Utah; Visualization and Computer Graphics, IEEE Transactions on Publication Date: July-September 2002 Volume: 8, Issue: 3 p 270-285, which is incorporated herein by reference.

Still referring to FIG. 1, according to processing step 130, at least one function is determined for associating each unitary image element of the selected type of region in the selected portion to another type of region of the at least three types of regions such that the at least one distribution of the selected type of regions in the selected portion is transposed into a corresponding distribution of the another type of region.

For the example of tagged material removal for virtual colonoscopy, the function that is determined is a function that allows to transpose the intensity distribution of the tagged regions into the intensity distribution of the air substance type region, as it will become apparent below with reference to FIGS. 5A to 6B.

As previously mentioned, in processing step 110, in a preferred embodiment, each of the portions of the different regions comprised in the resulting area may be large enough so as to be representative of the corresponding regions. Indeed, the skilled addressee will appreciate that the anatomical structures may typically be represented by a corresponding distribution having a typical predetermined shape, such as a Gaussian shape for example. Thus, the resulting area may be enlarged until a predetermined function such as a Gaussian function for instance may be suitably fitted onto the corresponding distribution.

In a preferred embodiment, in processing step 110, the determining of at least one function comprises determining an initial approximating function for approximating the corresponding distribution and determining a transposition function adapted for transposing the initial approximating function into the corresponding distribution of the another type of region.

In a preferred embodiment, the initial approximating may be determined such as described in Weisstein, Eric W. "Nonlinear Least Squares Fitting", from MathWorld—A Wolfram Web Resource, or Bates, D. M. and Watts, D. G., Nonlinear Regression and Its Applications. New York: Wiley, 198 or even An estimate of $\phi$ and $\omega$ yields from the 2000 run, Mihajlo Kornicer, Richard T. Jones, University of Connecticut, Storrs, Conn., Mar. 19, 2001, each of these references being incorporated herein by reference.

In the embodiment shown in FIG. 5B, the initial approximating function 516 is determined for approximating the peak 514. An illustrative embodiment may be found in The QtiPlot Handbook, Chapter 6; Analysis of data and curves, Multi-Peaks fitting, 2009, Ion Vasilief, which is incorporated by reference herein.

Still in a preferred embodiment, in processing step 110, an additional initial approximating function is determined for approximating the distribution of the another type of region.

In the embodiment shown in FIG. 5B, the initial approximating function is determined for approximating the peak 510.

Still in a preferred embodiment, the applying of the at least one function comprises applying the transposition function to thereby transpose the initial approximating function into the additional initial approximating function.

In one embodiment, each of the initial approximating function and the additional initial approximating function is selected from the group consisting of a laplacian function and a gaussian function.

The skilled addressee will appreciate that, in another embodiment, the determining of at least one function may comprise applying a Fourier transformation to the at least one distribution.

The skilled addressee will also appreciate that, in another embodiment, the determining of at least one function may comprise applying a parametric law to the at least one distribution. In one embodiment, the parametric law may be a quadratic law.

Details of such embodiments may be made obvious to someone skilled in the art by reading "Numerical Analysis for Chemical Engineers", Nikos Drakos, Computer Based Learning Unit, University of Leeds. & Ross Moore, Mathematics Department, Macquarie University, Sydney.

Still referring to FIG. 1, according to processing step 140, the at least one function is applied to each unitary image element of the selected type of region of the selected portion to thereby provide filtered image data.

In other words, the determined at least one function is used to assign, in the filtered image data, another value to each of the unitary image elements of the selected type of region, as it will be more detailed below.

For the application of tagged material removal for virtual colonoscopy, once the at least one function is determined, the skilled addressee will appreciate that the distribution of the selected type of region, i.e. the tagged region, is transposed or fitted onto the distribution of the air type regions, to thereby remove the tagged region in the filtered image data.

As previously described, FIG. 5A illustrates the image data of a portion of a colon 500, the image data comprising a biological tissues type region 502, an air type region 504 and two tagged substance type regions 506, 508 while FIG. 5B schematically shows the intensity distribution of the image data shown in FIG. 5A. The intensity distribution comprises a first peak 510 corresponding to the air type region 504, a second peak 512 corresponding to the biological tissues type region 502 and a third peak 514 corresponding to the tagged substance type regions 506, 508.

Figure 6A:
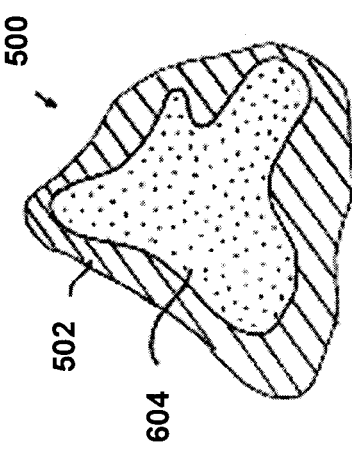
FIG. 6A is a schematic illustrating a sectional image of a colon once filtered according to the method illustrated in FIG. 1.
Figure 6B:
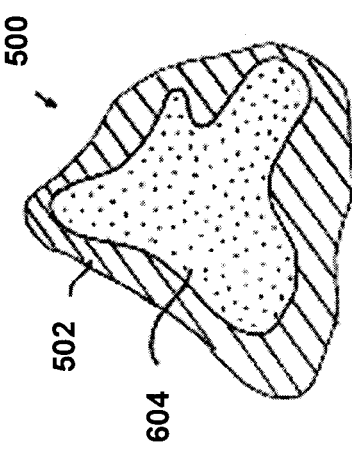
FIG. 6B is a schematic of the intensity distribution of the sectional image of FIG. 6A.

FIG. 6B shows the intensity distribution of the selected portion of the image data in the filtered image data once the at least one function has been applied to each of the unitary image elements of the selected portion of the original image data. In the illustrated case, the skilled addressee will appreciate that the third peak 514 corresponding to the tagged substance regions 506, 508 has been transposed onto the first peak 510 corresponding to the air type region 504.

The skilled addressee will appreciate that the term "transpose" should be understood such as in the musical meaning, i.e. to reproduce in a different key, by raising or lowering in pitch or, in other words, to perform a piece of music in a key other than the one in which it is written.

FIG. 6A shows the filtered image data once the processing step 140 has been performed. As illustrated, the two tagged substance type regions 506, 508 appearing in the original image data have been removed from the filtered image data. The values of the unitary image elements of these regions have been transposed so as to correspond to the values of the air type region 504.

Figure 4B:
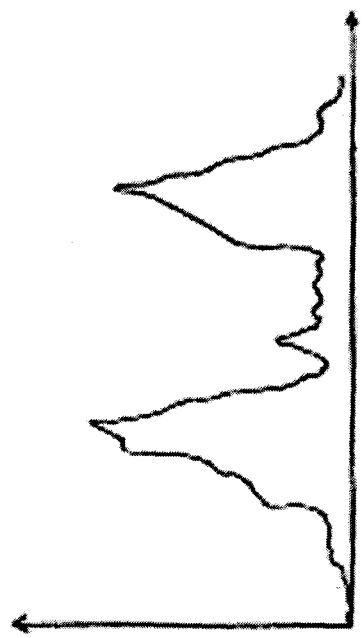
FIG. 4B is a schematic of the intensity distribution of the sectional image of FIG. 4A.
Figure 4A:
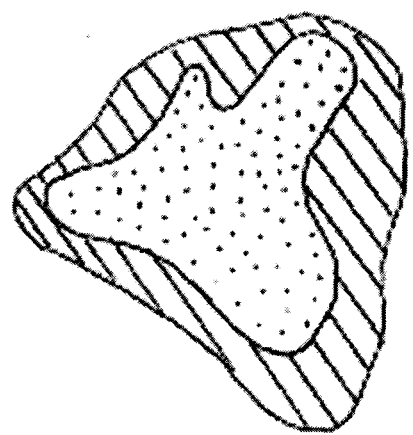
FIG. 4A is a schematic illustrating a sectional image of a clean colon.

The skilled addressee will thus appreciate that the above-described method allows to perform an electronic cleansing of the colon by suppressing tagged material. The filtered image data obtained with the method provide a representation of the colon without the tagged regions, similarly to a clean colon as the one shown in FIG. 4A.

The skilled addressee will also appreciate that the filtering of the tagged regions is obtained without segmenting any regions, which is of great advantage. Indeed, the method disclosed may be used as a pre-processing step prior to a subsequent processing such as a structure segmentation for example. In this case, the skilled addressee will appreciate that it is particularly advantageous to provide filtered image data that have not been segmented prior to the subsequent processing.

Figure 8A:
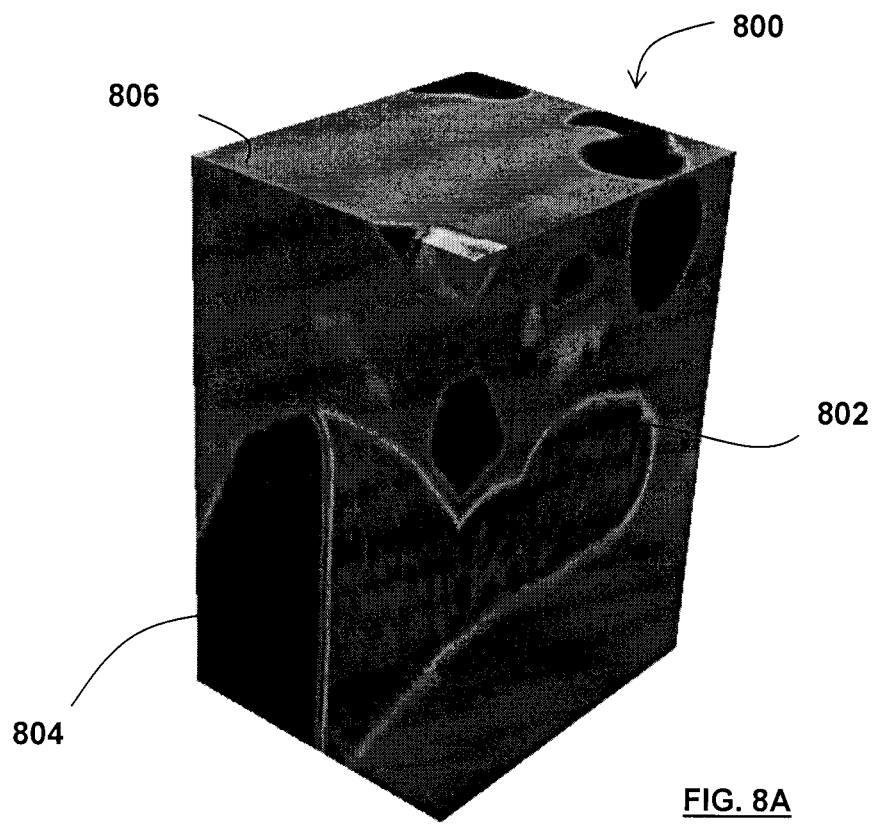
FIG. 8A shows a selected portion of image data, according to an embodiment.

FIG. 8A shows an exemplary selected portion 800 of the image data. The selected portion 800 is a 3D portion and comprises each of the at least three types of regions, that is a tagged type regions 802, an air type region 804 and another region corresponding to a biological tissue type region 806.

Figure 8B:
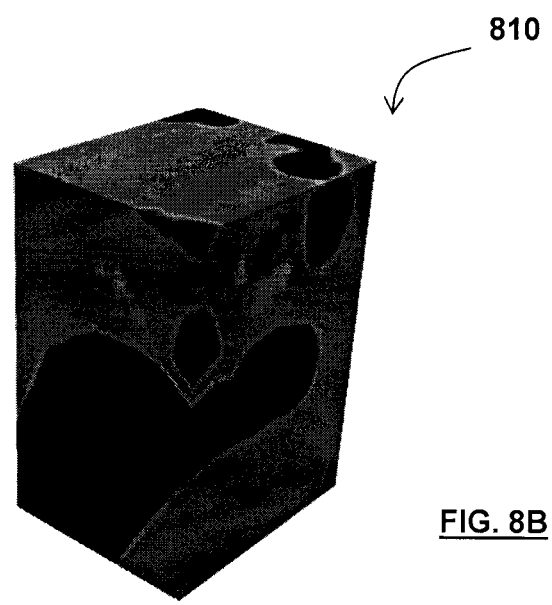
FIG. 8B shows filtered image data of the selected portion shown in FIG. 8A.

FIG. 8B shows the filtered image 810 obtained with the above described method for filtering image data. The skilled addressee will appreciate that the tagged type region 802 has been filtered and replaced with an air type region.

Figure 8C:
FIG. 8C is an enlarged portion of FIG. 8A.
Figure 8D:
FIG. 8D is an enlarged portion of FIG. 8B.

FIG. 8C shows an enlarged portion of FIG. 8A comprising the tagged type region 802 while FIG. 8D shows the same enlarged portion once the filtering has been done. The skilled addressee will appreciate that the interface between the tagged type region 802 and the biological tissue type region 806 has not been modified nor altered, which is of great advantage for detecting small lesions, as mentioned above.

Figure 9:
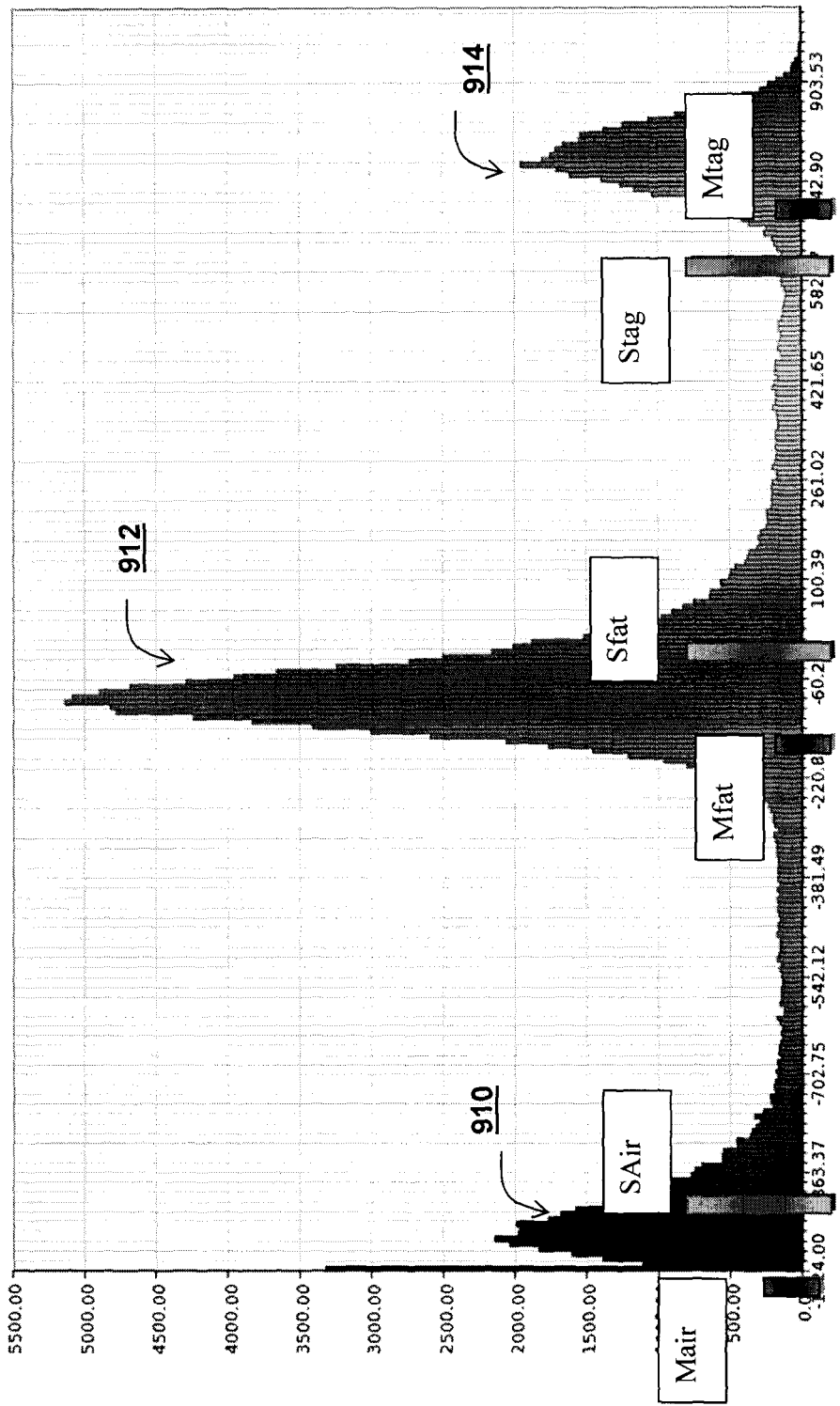
FIG. 9 shows the intensity distribution of the selected portion of FIG. 8A.

FIG. 9 shows the intensity distribution of the selected portion 800 of the image data shown in FIG. 8A. As illustrated, the intensity distribution comprises a first peak 910 corresponding to the air type region 804, a second peak 912 corresponding to the biological tissues type region 806 and a third peak 914 corresponding to the tagged substance type region 802.

According to an embodiment of the method for filtering image data previously described, an intensity distribution is determined for each of the three types of regions in the selected portion. The skilled addressee will appreciate that in the case of virtual colonoscopy, the method may be implemented for a plurality of selected portions of the image data in order to filter each of the tagged type regions in the image data.

Therefore, an intensity distribution is determined for each tagged type region, each of these intensity distributions being specific to each tagged type region. Similarly, an intensity distribution is determined for each air type region, each of these intensity distributions being specific to each air type region.

In one embodiment, each distribution of each air type region may be cumulated in order to provide a representative general distribution of the air type regions specific to the image data of a given patient. At this point, in this embodiment, each distribution of each tagged type region of the image data may be transposed into the representative general distribution of the air type region.

In a further embodiment, each distribution of each biological tissue type region may be cumulated in order to provide a representative general distribution of the biological tissue type regions specific to the image data of a given patient.

The skilled addressee will nevertheless appreciate that, in a preferred embodiment, the method for filtering image data relies on the specific distribution of each given region.

In one embodiment, each specific distribution of the air type regions and the tagged type regions may be compared to the respective corresponding representative general distributions. In the case a given specific distribution seems to be not representative, i.e. the specific distribution greatly differs from the corresponding general distribution, various techniques may be considered.

In one embodiment, the representative general distribution may be used in place of the specific distribution.

In another embodiment, the corresponding selected portion of the image data may be enlarged in order to increase the statistical information contained therein. This enlarging may be performed until the specific distribution seems to be representative, compared to the corresponding representative general distribution.

In the case the specific distribution still greatly differs from the representative general distribution and/or the selected portion of the image data may not be enlarged anymore, the representative general distribution may be used.

In one embodiment, predetermined general distributions may be used in the case the corresponding representative general distribution may not be obtained.

The skilled addressee will appreciate that, in a preferred embodiment, the representative general distributions of the air type regions and biological tissue type regions may be used.

Once the distributions have been determined in the selected portion of the image data, the distribution of the tagged type region is transposed into the distribution of the air type region.

Referring again to FIG. 9, each unitary image element whose intensity is above Mtag is considered to extend in a tagged region. Each unitary image element whose intensity is comprised below Stag and above Sfat is considered to extend proximate to an interface between a tagged type region and the mucosa of the colon.

FIGS. 10A to 10C show how the distribution corresponding to a tagged type region is transposed into the distribution corresponding to an air type region. The skilled addressee will appreciate that Mfat may be used as a pivot for performing the transposition although other arrangements may be considered.

Figure 11:
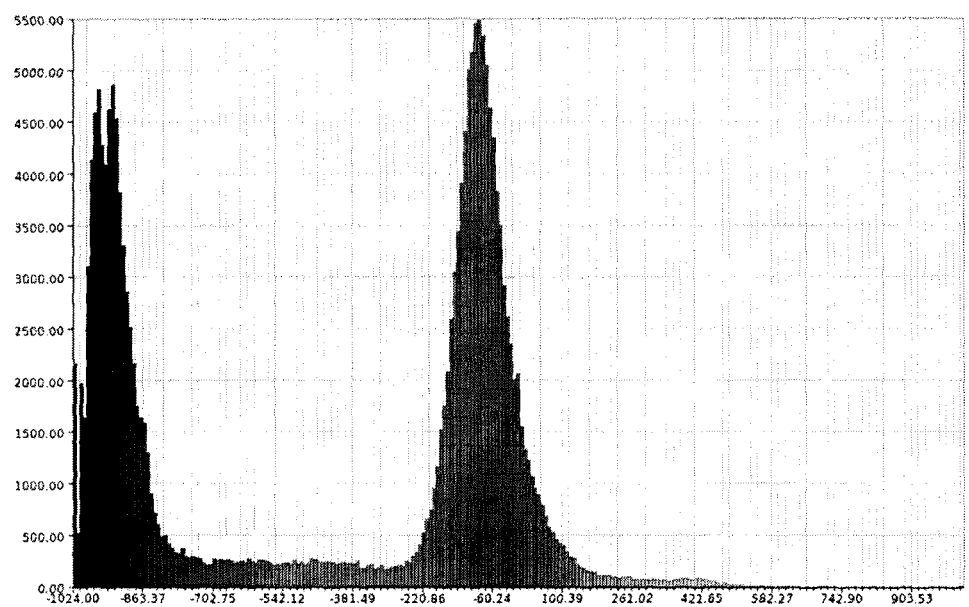
FIG. 11 shows the resulting distribution of the selected portion of FIG. 8A once the filtering has been performed, according to one embodiment.

FIG. 11 shows the resulting distribution once the distribution of the tagged type region has been transposed into the distribution of the air type region. The skilled addressee will appreciate that in FIG. 11, the properties of the air distribution and the biological tissue distribution have been preserved during the transposition process. In other words, in the case of Gaussian functions, the standard deviations of each distribution are the same as the ones of FIG. 9.

It is worth mentioning that in the above example, gaussian functions have been chosen but other types of functions may be considered. Moreover, even in the case of a Gaussian function, other properties than sigma (Stag for example) and mu (Mtag for example) may be chosen to perform the transposition. The skilled addressee will also appreciate that others parameters allowing to characterize the distributions may be used.

The skilled addressee will also appreciate that in the above described example, the transposition may be considered as a process based on the relative connectivity of the elements. Indeed, a unitary image element representing a biological tissue type region which is not connected to a tagged type region will not be transposed.

FIGS. 12 to 15 more clearly illustrates how the transposition may be performed, in one embodiment.

Figure 12:
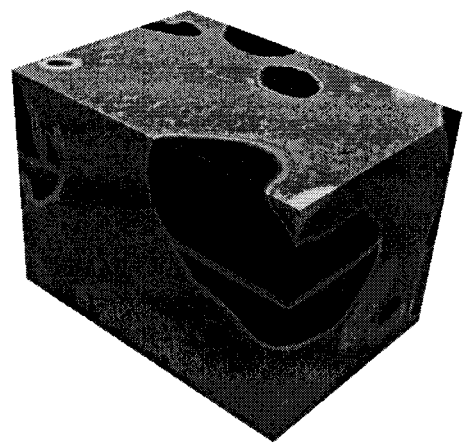
FIG. 12 shows a selected portion of image data, according to an embodiment.
Figure 13:
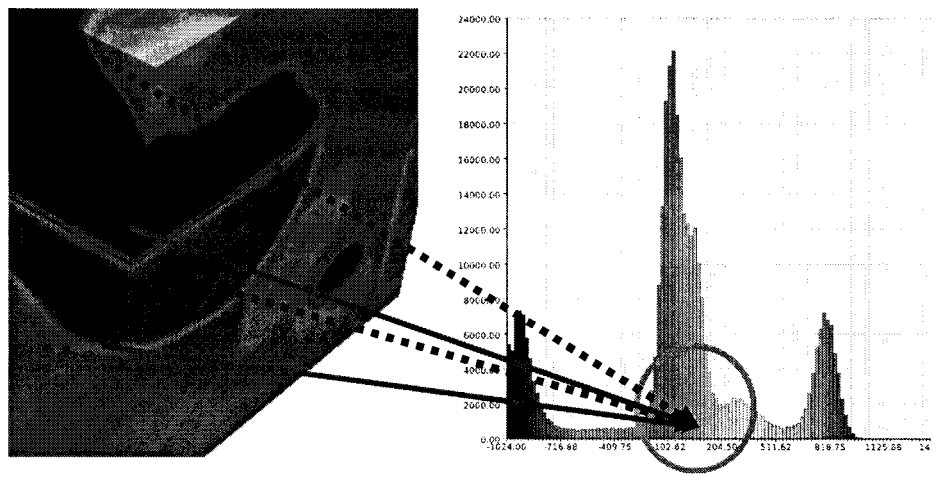
FIG. 13 illustrates the intensity distribution of the selected portion of image data of FIG. 12.

Referring to FIGS. 12 and 13, there is shown a selected portion of the image data and the corresponding intensity distribution. In this illustrative example, the gray continuous arrows depict the contribution of elements connected to the region of interest to the overall local distribution and that should be transposed. These elements comprise the interfaces between an air type region and a tagged type region and the interfaces between the mucosa of the colon and a tagged type region. The black dashed arrows depict the contribution of elements that are not connected to the region of interest and that should not be transposed but nevertheless remain of great interest for describing the surrounding environment. These elements comprise the surrounding biological tissues.

Figure 14:
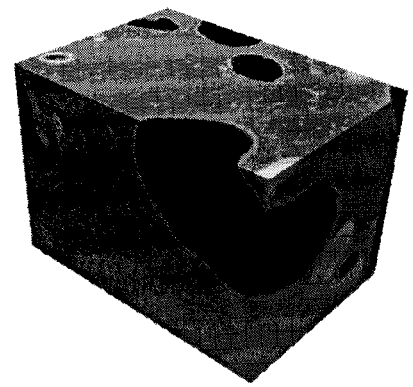
FIG. 14 shows filtered image data of the selected portion shown in FIG. 12.
Figure 15:
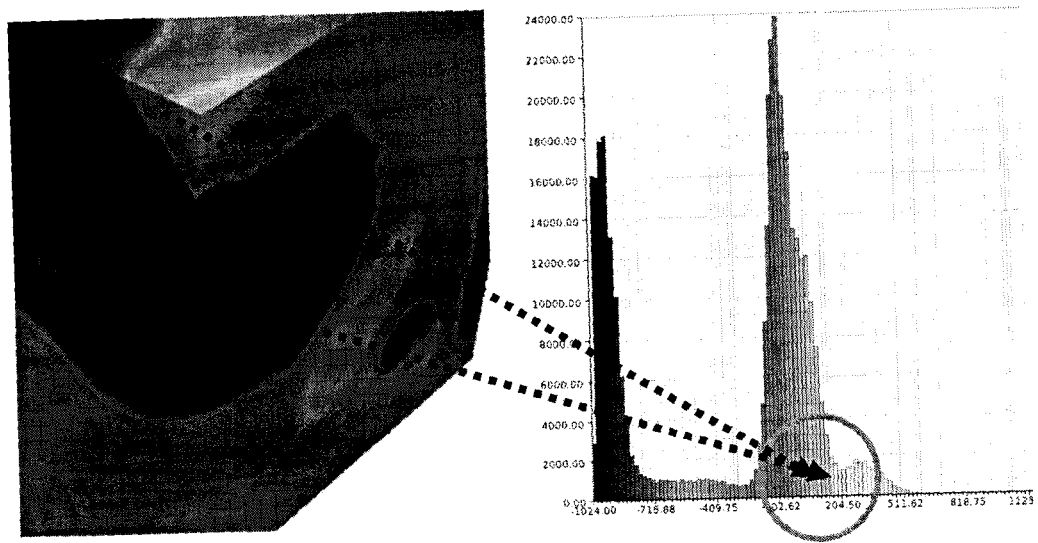
FIG. 15 shows the resulting distribution of the selected portion of FIG. 12 once the filtering has been performed, according to one embodiment.

FIGS. 14 and 15 show the filtered image data once the transposition has been performed and the corresponding intensity distribution. It is worth noting that the tagged type region has been transposed while the elements not connected to the region of interest to be transposed have not been transposed and thus remain unchanged. This is clearly illustrated in FIGS. 14 and 15. The skilled addressee will appreciate that the distribution of the overall transposed portion of the image substantially depicts the same characteristics, but one can realize that there is an attenuation due to the transposition of the relevant elements.

The skilled addressee will thus appreciate that the relations between the different elements, i.e. their relative connectivity, are taken into consideration during the transposition.

Moreover, the skilled addressee will also appreciate that in the above described example, the transposition is performed according to a linear model but various other model may be considered to perform the transposition.

Figure 3A:
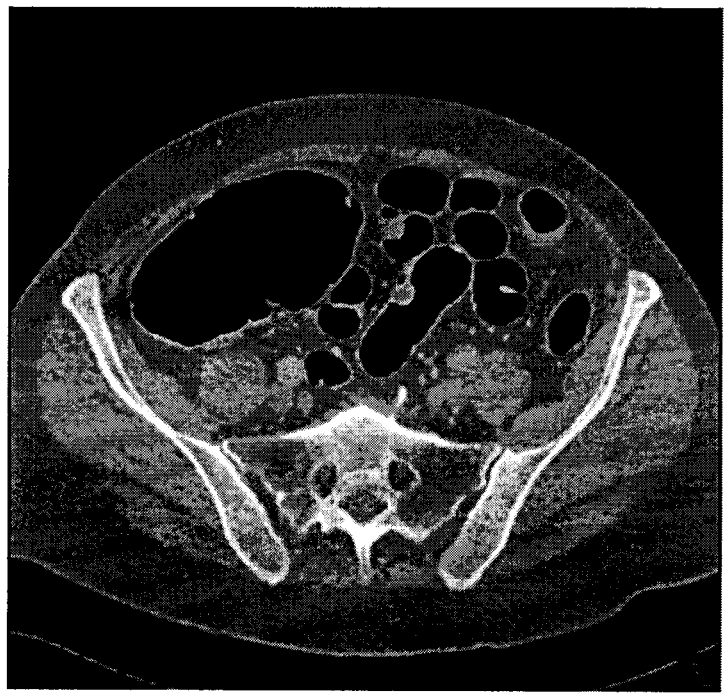
FIG. 3A shows a portion of filtered image data.
Figure 3B:
FIG. 3B shows a 3D representation of a portion of the image data of FIG. 3A.
Figure 3C:
FIG. 3C is a 3D representation of a colon of a patient.

In one embodiment, the method for filtering image data may further comprises displaying the filtered image data. In the case the image data are representative of a portion of a colon, the method for filtering image data further comprises displaying a three dimensional rendering of the portion of the colon. FIGS. 3A and 3B respectively show a portion of the image data 300 as well as a three dimensional rendering 302 of the portion of the colon illustrated in FIG. 3C.

In one embodiment, the method for filtering image data may further comprise providing the filtered image data to a volume rendering engine for 3D visualization.

In one embodiment, the method for filtering image data further comprises providing the filtered image data to a computer-aided detection unit for abnormalities detection, as detailed thereinafter.

The skilled addressee will appreciate that the method for filtering image data as previously described may be particularly useful as a pre-processing step prior to perform a virtual colonoscopy but other types of endoscopies may also be considered. It should therefore be understood that the filtering method described above is not limited to the applications of colon image filtering but is rather directed to a general filtering method well adapted for anatomical structures comprising at least two phases. For non-limitative examples, the method may be useful for examination of abdominal aneurysms and neuro aneurysms.

The skilled addressee will also appreciate that the described filtering method is not limited to applications of examination of different human anatomical structures or animal anatomical structures. Indeed, it may also be applied to any type of image, including single 2D image, in order to perform an image filtering or image correction. For example, the method may be used for enclosed object examination for which a real visual inspection may not be performed. It may also be useful for filtering satellite images and radar images as non-limitative examples.

According to another aspect, there is also provided a system for filtering image data having at least three types of distinct regions from a selected type of region, each of the at least three types of distinct regions being characterized by a plurality of unitary image elements.

Figure 2:
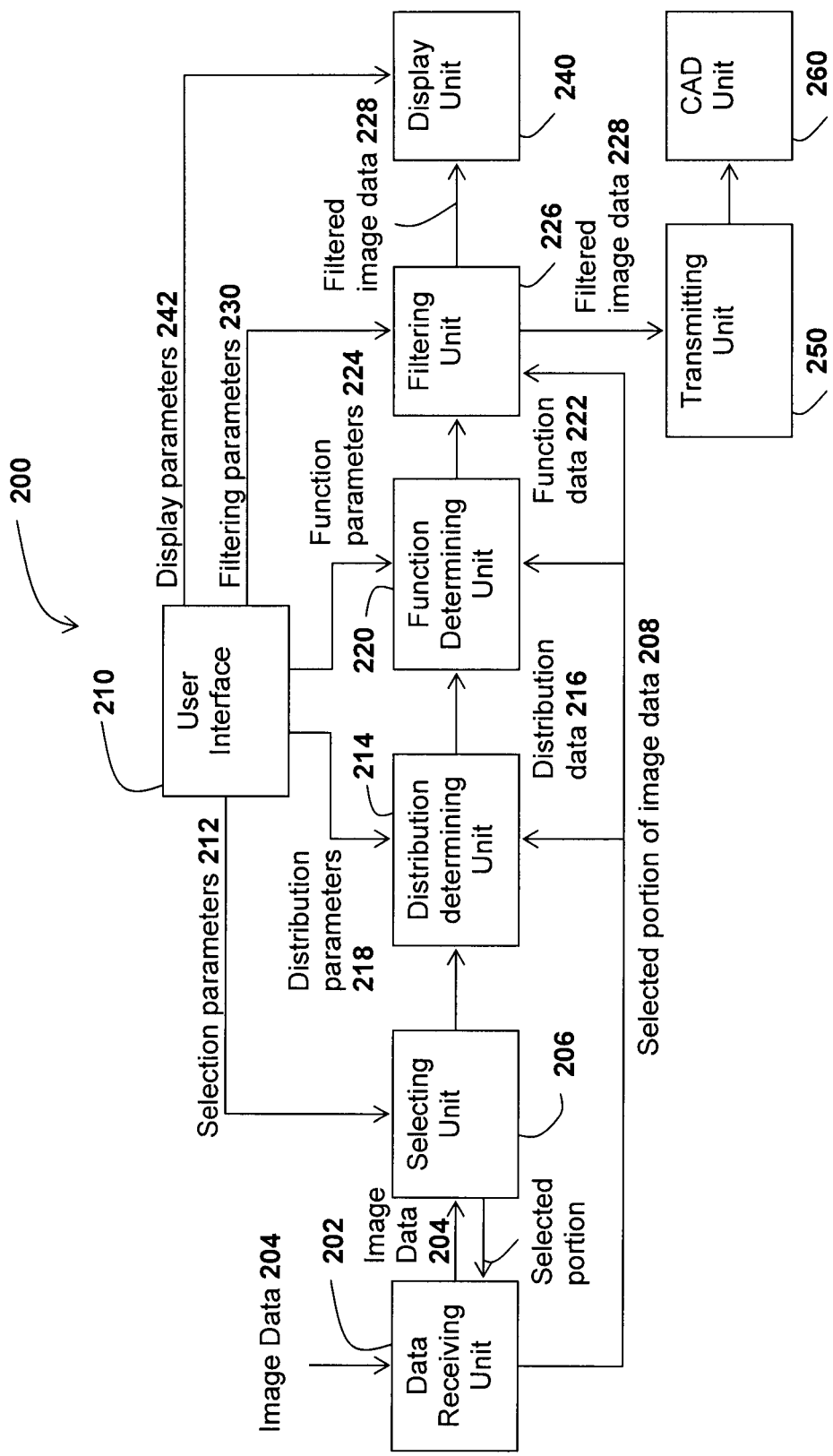
FIG. 2 is a block diagram of one embodiment of a system for filtering image data, according to the invention.

Referring to FIG. 2, the system 200 comprises a data receiving unit 202 for receiving the image data 204 and a selecting unit 206 operatively coupled to the data receiving unit 202 for selecting a portion of the image data 204 comprising at least a corresponding portion of each of the at least three types of regions and providing a selected portion 208 of the image data 204.

In one embodiment, the system 200 may comprise a user interface 210 operatively connected to the selecting unit 206 for providing selection parameters 212 to thereby select the portion 208 of the image data 204. In a preferred embodiment, the portion 208 of the image data 204 is selected automatically, without user's intervention.

An exemplary method for such automatic process has been described in "Automated seed placement for colon segmentation in computed tomography colonography", *Academic Radiology*, Volume 12, Issue 2, Pages 182-190 G. Iordanescu, P. Pickhardt, J. Choi, R. Summers February 2005, and in "Automatic segmentation of the colon for virtual colonoscopy", Computerized Medical Imaging and Graphics Volume 24, Issue 1, February 2000, Pages 1-9, C. L. Wyatt, Y. Ge and D. J. Vining.

Still referring to FIG. 2, the system 200 comprises a distribution determining unit 214 operatively coupled to at least one of the selecting unit 206 and the data receiving unit 202 for determining at least one distribution for each of the at least three types of regions in the selected portion 208 and providing at least one determined distribution, i.e. the distribution data 216, for each of the at least three types of regions in the selected portion 208.

In one embodiment, the user interface 210 is operatively connected to the distribution determining unit 214 and is used for providing distribution parameters 218 thereto. The distribution parameters 218 may comprise, in one embodiment, a number and a type of distributions to determine, as described above. In a preferred embodiment, the distribution parameters 218 are predetermined and the at least one distribution is then determined automatically, without user's intervention.

The system 200 further comprises a function determining unit 220 operatively coupled to the distribution determining unit 214 for determining at least one function for associating each unitary image element of the selected type of region in the selected portion 208 to another type of region of the at least three types of regions such that the at least one determined distribution of the selected type of regions in the selected portion 208 is transposed into a corresponding distribution of the another type of region.

The function determining unit 220 receives the distribution data 216 from the distribution determining unit 214 and provides function data 222 in response thereto.

In one embodiment, the function determining unit 220 may be operatively connected to the user interface 210 for receiving function parameters 224 such as, in one embodiment, a number and a type of function to determine. In a preferred embodiment, the function parameters 224 are predetermined and the function is then determined automatically, without user's intervention.

In a preferred embodiment, the function determining unit 220 comprises a module (not shown) for determining an initial approximating function to approximate the corresponding distribution and a module (not shown) for determining a transposition function adapted to transpose the initial approximating function into the corresponding distribution of the another type of region.

Still in a preferred embodiment, the function determining unit 220 comprises a module (not shown) for determining an additional initial approximating function to approximate the distribution of the another type of region.

The system 200 also comprises a filtering unit 226 operatively coupled to the function determining unit 220 for applying the at least one function to each unitary image element of the selected type of region of the selected portion 208 to thereby provide filtered image data 228.

The filtering unit 226 receives the function data 222 from the function determining unit 220 and the image data 204 from the data receiving unit 202 and then provides the filtered image data 228 in response thereto.

In a preferred embodiment, the function data 222 comprises transposition function data and the filtering unit 226 applies the received transposition function to thereby transpose the initial approximating function into the additional initial approximating function, as previously explained.

In one embodiment, the filtering unit 226 may be operatively connected to the user interface 210 for receiving filtering parameters 230. In a preferred embodiment, the filtering parameters 230 are predetermined and the determined function is applied automatically, without user's intervention.

The skilled addressee will appreciate that, in one embodiment, the system may be entirely automated. In this case, the predetermined parameters may comprise the number of types of distinct regions, three in an exemplary embodiment, and parameters concerning the distribution of each type of distinct regions, a Gaussian shape in an exemplary embodiment. Still in an exemplary embodiment and according to the type of image used, a predetermined mean value may be assigned for each Gaussian initial approximating function. For example, for images obtained by "CT scan Rx", the mean value may be −800 Hu for an air type region, +300 Hu for a tagged substance type region and +50 Hu for the remaining regions, i.e. the biological tissues. The skilled addressee will appreciate that various other arrangements may be considered.

Still referring to FIG. 2, in one embodiment, the system 200 may further comprises an optional display unit 240 operatively coupled to the filtering unit 226 for displaying the filtered image data 228 to the user. In a further embodiment, the display unit 240 may be connected to the user interface 210 for receiving display parameters 242.

In another further embodiment, the system 200 further comprises a transmitting unit 250 coupled to the filtering unit 226 for transmitting the filtered image data 228 either to a computer-aided detection unit 260 for abnormalities detection or to a computer-aided diagnosis unit (not shown) for abnormalities diagnosis. The transmitting unit 250 may comprise a wireless module (not shown) for providing a wireless transmission of the filtered image data 228. The skilled addressee will appreciate that the filtered image data may be transmitted using the wireless module according to various protocols without departing from the scope of this application. The skilled addressee will also appreciate that a wired transmission as well as an internet transmission may be used.

The system for filtering image data as previously described is of great advantage since it may allow a remote processing of the image data. Indeed, the image data may be acquired at the clinic or the hospital equipped with imaging devices, sent via a public network to a remote processing center and processed at the processing center. The filtered image data may then be sent to the hospital for a visual analysis by a doctor.

Alternatively, the skilled addressee will appreciate that the system for filtering image data may be integrated to the imaging device or be operatively connected thereto.

As previously mentioned, the system for filtering image data may be particularly useful for suppressing tagged material in virtual colonoscopies.

The skilled addressee will also appreciate that, in one embodiment, the method for filtering image data may be embedded in a computer program running on a processing device. The computer program may comprise instructions recorded on a machine readable medium for performing the above-described method for filtering image data.

According to another aspect, there is also provided a method of doing business in filtering image data according to the method for filtering image data previously described, wherein the image data are filtered for a fee.

According to another aspect, there is also provided a method of doing business in filtering image data, the method comprising receiving the image data; performing the method for filtering image data as previously described; and providing the filtered image for a fee.

According to another aspect, there is also provided a method of doing business in filtering image data, the method comprising providing by a provider a system for filtering image data as previously described to a third party; operating the system, wherein the operating is done by a third party for a fee; and reconveying by the third party at least a portion of the fee to the provider.

According to another aspect, there is also provided a method of doing business in filtering image data, the method comprising providing a tagging agent; defining a tagging agent distribution associated to the tagging agent; providing a system for filtering image data wherein the system is customized according to the tagging agent distribution; performing the method for filtering image data as previously described wherein the image data are obtained with the tagging agent; and providing the filtered image for a fee.

According to another aspect, there is also provided a method of doing business in filtering image data, the method comprising providing a tagging agent; defining a tagging agent distribution associated to the tagging agent; providing by a provider a system for filtering image data to a third party, the system being customized according to the tagging agent distribution; operating the system, wherein the operating is done by a third party for a fee; and reconveying by the third party at least a portion of the fee to the provider.

According to another aspect, there is also provided the use of the system for filtering image data for suppressing tagged material in a virtual colonoscopy involving Iodine-based tagging agents.

According to another aspect, there is also provided the use of the system for filtering image data for suppressing tagged material in a virtual colonoscopy involving Barium-based tagging agents.

It will be appreciated that the system for filtering image data described herein may be operated by the owner of the system. Alternatively, the system may be operated by a third party for a fee. In one embodiment, the fee may be a share of the revenues while in an alternative embodiment, the fee may comprise a fixed fees.

Figure 7:
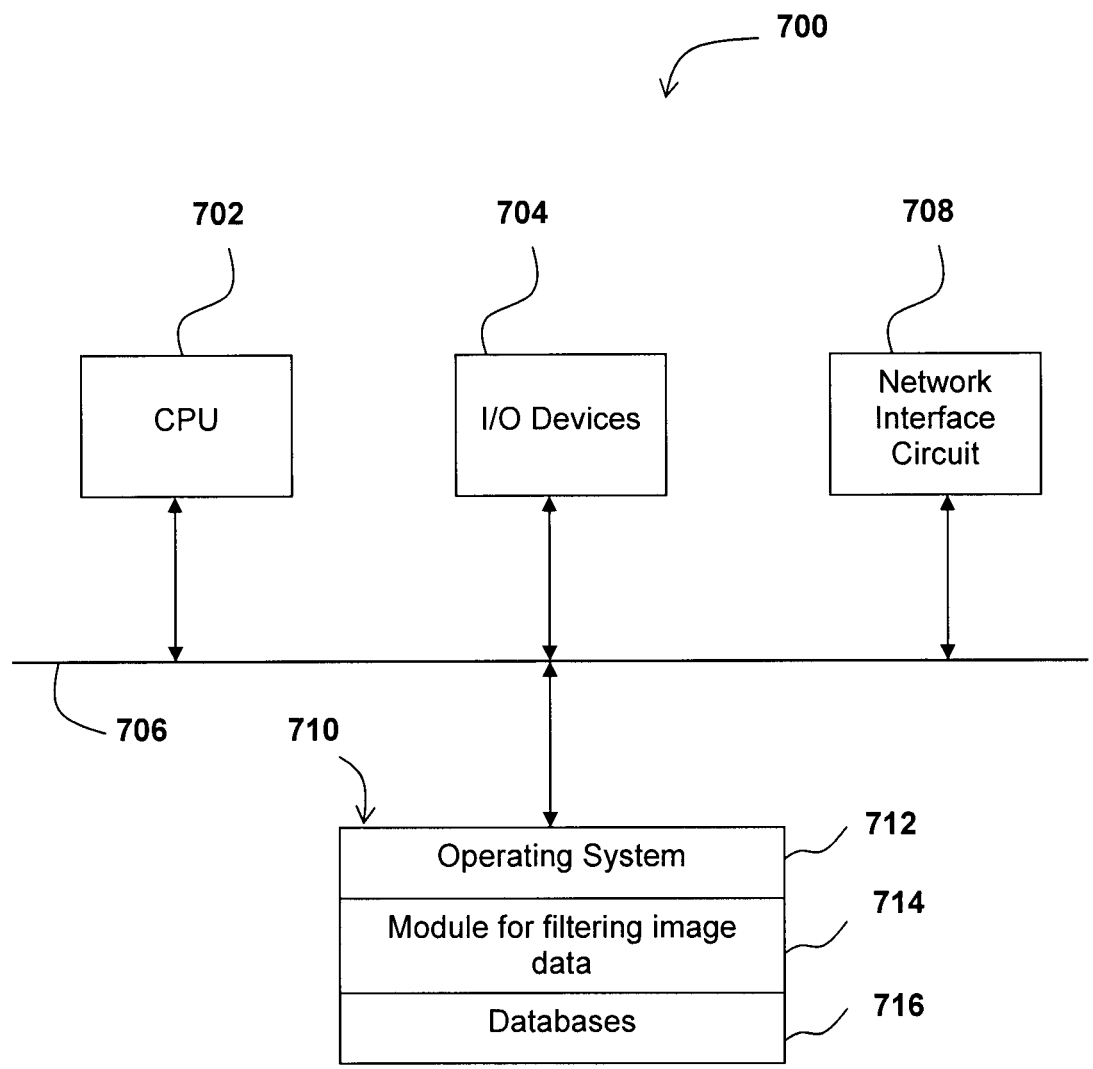
FIG. 7 is a block diagram which shows an embodiment of a processing device in which the method for filtering image data may be implemented.

Now referring to FIG. 7, there is shown an embodiment of a processing device 700 in which the method for filtering image data may be advantageously used.

The processing device 700 comprises a central processing unit 702, I/O devices 704, a network interface circuit 708, a data bus 706 and a memory 710. The central processing unit 702, the I/O devices 704, the network interface circuit 708 and the memory 710 are operatively coupled using the data bus 706.

More precisely, the central processing unit 702 is adapted for processing data instructions. The network interface circuit 708 is adapted for operatively connecting the processing device 700 to another processing device (not shown) via a data network (not shown). The skilled addressee will appreciate that various embodiments of the network interface circuit 708 may be provided. Moreover, the skilled addressee will also appreciate that the network interface circuit 708 may operate according to various communication protocols such as TCP/IP for instance.

The I/O devices 704 are used for enabling a user to interact with the processing device 700. The skilled addressee will appreciate that various embodiments of the I/O devices 704 may be used. For example, the I/O devices 704 may comprise at least one of a keyboard, a screen and a mouse.

The skilled addressee will appreciate that various embodiments of the data bus 706 may be provided.

It will also be appreciated that various embodiments of the memory 710 may be provided. Moreover, it will be appreciated that the memory 710 may be used to store in one embodiment an operating system 712, a module for filtering image data 714 and databases 716 used for operating the module for filtering image data 714.

The skilled addressee will appreciate that the operating system 712 is used for managing the interactions between the central processing unit 702, the I/O devices 704, the network interface circuit 708, the data bus 706 and the memory 710.

Although the above description relates to specific preferred embodiments as presently contemplated by the inventor, it will be understood that the invention in its broad aspect includes mechanical and functional equivalents of the elements described herein. For example, the method may be applied to the examination of different human anatomical structures as well as animal structures. It may also be applied to enclosed object examination for which a real visual inspection may not be performed.

What is claimed is:

1. A method for filtering image data having at least three types of distinct regions from a selected type of region, each of the at least three types of distinct regions being characterized by a plurality of unitary image elements, the method comprising:

providing said image data;

selecting a portion of said image data comprising at least a corresponding portion of at least two of said at least three types of regions, said at least two types of regions comprising the selected type of region;

determining at least one distribution for at least one of said at least two types of regions in said selected portion, wherein said step of determining at least one distribution is performed without any prior segmentation or classification of the image data;

determining at least one function for associating each unitary image element of said selected type of region in said selected portion to another type of region of the at least three types of regions such that said at least one distribution of said selected type of regions in said selected portion is transposed into a corresponding distribution of said another type of region; and applying said at least one function to each unitary image element of said selected type of region of said selected portion to thereby provide filtered image data.

2. The method for filtering image data according to claim 1, wherein said corresponding distribution of said another type of region is determined in said selected portion.

3. The method for filtering image data according to claim 1, wherein said corresponding distribution of said another type of region is determined in said image data.

4. The method for filtering image data according to claim 1, wherein said image data are representative of an anatomic structure.

5. The method for filtering image data according to claim 4, wherein said anatomic structure comprises a portion of a colon.

6. The method for filtering image data according to claim 4, further comprising displaying a three dimensional rendering of said anatomic structure.

7. The method for filtering image data according to claim 1, wherein each of said at least three types of distinct regions respectively comprises a first substance type region, a second substance type region and a third substance type region.

8. The method for filtering image data according to claim 7, wherein each of said at least three types of distinct regions respectively comprises an air type region, a tagged substance type region and a biological tissues type region.

9. The method for filtering image data according to claim 8, wherein said filtered image data comprise at least an air type region and a biological tissues type region.

10. The method for filtering image data according to claim 1, wherein said selected portion of said image data comprises a corresponding region of said selected type of region.

11. The method for filtering image data according to claim 1, wherein said selecting a portion of said image comprises selecting one of said regions and selecting an immediate neighboring region until a resulting area comprises said at least two types of regions.

12. The method for filtering image data according to claim 11, wherein an immediate neighboring region is selected until said resulting area comprises a representative portion of each of said at least two types of regions.

13. The method for filtering image data according to claim 11, wherein an immediate neighboring region is selected until said resulting area comprises a representative portion of each of said at least three types of regions.

14. The method for filtering image data according to claim 1, wherein said selecting a portion of said image comprises selecting one of said regions and selecting an immediate neighboring region until a resulting area comprises said at least three types of regions.

15. The method for filtering image data according to claim 1, wherein said determining at least one distribution comprises determining an intensity derivative distribution of a representative part of the unitary image elements corresponding to said selected portion.

16. The method for filtering image data according to claim 1, wherein said determining at least one distribution comprises determining a plurality of distributions selected from a group consisting of an intensity distribution of a representative part of the corresponding unitary image elements, a gradient distribution of a representative part of the corresponding unitary image elements and an intensity derivative distribution of a representative part of the corresponding unitary image elements.

17. The method for filtering image data according to claim 1, wherein said determining at least one function comprises determining an initial approximating function for approximating the corresponding distribution and determining a transposition function adapted for transposing the initial approximating function into the corresponding distribution of said another type of region.

18. The method for filtering image data according to claim 17, further comprising determining an additional initial function for approximating the distribution of said another type of region, and wherein the applying of said at least one function comprises applying the transposition function to thereby transpose the initial function into the additional initial function.

19. The method for filtering image data according to claim 1, further comprising displaying said filtered image data.

20. The method for filtering image data according to claim 1, further comprising providing said filtered image data to a computer-aided detection unit for abnormalities detection.

21. The method for filtering image data according to claim 1, further comprising providing said filtered image data to a volume rendering engine for 3D visualization.

22. A system for filtering image data having at least three types of distinct regions from a selected type of region, each of the at least three types of distinct regions being characterized by a plurality of unitary image elements, the system comprising:
   a data receiving unit for receiving said image data;
   a selecting unit coupled to the data receiving unit for selecting a portion of said image data comprising at least a corresponding portion of at least two of said at least three types of regions, said at least two types of region comprising the selected type of region, the selecting unit providing a selected portion of said image data;
   a distribution determining unit coupled to at least one of the selecting unit and the data receiving unit for determining at least one distribution for at least one of said at least two types of regions in said selected portion and providing at least one determined distribution for the at least one of said at least two types of regions in said selected portion, wherein said determining at least one distribution is performed without any prior segmentation or classification of the image data;
   a function determining unit coupled to the distribution determining unit for determining at least one function for associating each unitary image element of said selected type of region in said selected portion to another type of region of the at least three types of regions such that said at least one determined distribution of said selected type of regions in said selected portion is transposed into a corresponding distribution of said another type of region; and
   a filtering unit coupled to the function determining unit and the data receiving unit for applying said at least one function to each unitary image element of said selected type of region of said selected portion to thereby provide filtered image data.

23. The system for filtering image data according to claim 22, further comprising a display unit coupled to the filtering unit for displaying said filtered image data to an operator.

24. The system for filtering image data according claim 22, further comprising a transmitting unit coupled to the filtering unit for transmitting said filtered image data to a computer-aided detection unit for abnormalities detection.

25. The system for filtering image data according to claim 22, wherein said function determining unit comprises a first module for determining an initial approximating function to approximate the corresponding distribution and a second module for determining a transposition function adapted to transpose the initial approximating function into the corresponding distribution of the another type of region.

* * * * *